United States Patent
Stelzig et al.

(10) Patent No.: US 10,072,212 B2
(45) Date of Patent: Sep. 11, 2018

(54) DOPO-BASED HYBRID FLAME RETARDANTS

(71) Applicant: EMPA EIDGENOSSISCHE MATERIAL-PRUFUNGS- UND FORSCHUNGSANSTALT, Dubendorf (CH)

(72) Inventors: Timea Stelzig, Radolfzell (DE); Lea Bommer, Bronschhofen (CH); Sabyasachi Gaan, Gossau (CH); Aleksandra Buczko, Stary Dzikow (PL); Rudolf Hufenus, Abtwil (CH); Giuseppino Fortunato, St. Gallen (CH); Benno Wüst, Thal (CH); Pierluigi Barbadoro, Flawil (CH)

(73) Assignee: EMPA Eidgenossische Materialprufungs-Und Forschungsanstalt (CH)

(*) Notice: Subject to any disclaimer, the term of this patent is extended or adjusted under 35 U.S.C. 154(b) by 67 days.

(21) Appl. No.: 15/126,433

(22) PCT Filed: Mar. 16, 2015

(86) PCT No.: PCT/EP2015/055433
§ 371 (c)(1),
(2) Date: Sep. 15, 2016

(87) PCT Pub. No.: WO2015/140105
PCT Pub. Date: Sep. 24, 2015

(65) Prior Publication Data
US 2017/0081590 A1    Mar. 23, 2017

(30) Foreign Application Priority Data

Mar. 17, 2014 (EP) .................................... 14160392

(51) Int. Cl.
*C07F 9/6574* (2006.01)
*C09K 21/12* (2006.01)
(Continued)

(52) U.S. Cl.
CPC .......... *C09K 21/12* (2013.01); *C07F 9/65748* (2013.01); *C07F 9/657181* (2013.01);
(Continued)

(58) Field of Classification Search
CPC ................................................... C07F 9/6574
(Continued)

(56) References Cited

U.S. PATENT DOCUMENTS 4,228,064 A    10/1980  Izawa et al.
4,801,625 A    1/1989   Parr et al.
(Continued)

FOREIGN PATENT DOCUMENTS

DE    10330774    3/2005
EP    1506968     9/2009
(Continued)

OTHER PUBLICATIONS

New Phosphorus-Containing Quinone Derivatives II: Tri- and Tetraphosphorylated Quinone Derivatives; Patrick Müller et al., Heteroatom Chemistry, vol. 24, No. 4, 2013.
(Continued)

*Primary Examiner* — Duc Truong
(74) *Attorney, Agent, or Firm* — George Pappas

(57) ABSTRACT

The invention relates to novel and improved halogen-free flame retardant compounds having the structure of Formula (I): wherein: $R^1$ and $R^2$ are independently hydrogen, $C_1$-$C_6$ alkyl, —$P(O)(OR^3)_2$, —$P(O)OR^3R^4$, or —$P(O)R^3_2$, wherein $R^3$ and $R^4$ are independently $C_1$-$C_4$ alkyl, $C_6$-$C_{12}$ aryl, $C_7$-$C_{15}$ aralkyl or $C_7$-$C_{15}$ alkaryl; or $R^1$ and $R^2$ taken together form an unsaturated cyclic ring, which is optionally substi-
(Continued)

tuted by an alkyl group; each k is independently an integer from 1 to 2; each X is independently oxygen (O) or sulphur (S); v is 0 or 1; each Y is independently $C_1$-$C_4$ alkylene, $C_6$ arylene, $C_7$-$C_{15}$ aralkylene, $C_7$-$C_{15}$ alkarylene, oxygen (O), nitrogen (NR), wherein R is H or $C_1$-$C_4$ alkyl; n is 0, 1 or 2 with the proviso that n is 1 when Y is oxygen (O) or nitrogen (NR); each Z is independently $C_1$-$C_4$ alkylene, $C_6$ arylene, $C_7$-$C_{15}$ aralkylene or $C_7$-$C_{15}$ alkarylene; m is independently 0, 1 or 2; with the proviso that when Y is oxygen (O) or nitrogen (N), m cannot be 0; each Q is independently $C_1$-$C_4$ alkylene; t is an integer from 1 to 2; W is oxygen (O) or sulphur (S). The compounds are particularly suited as flame retardant additives for thermoplastic polyesters.

20 Claims, 1 Drawing Sheet

(51) Int. Cl.
| | |
|---|---|
| *C08L 69/00* | (2006.01) |
| *C07F 9/6571* | (2006.01) |
| *C08K 5/3492* | (2006.01) |
| *C08K 5/5373* | (2006.01) |
| *C08K 5/5398* | (2006.01) |
| *D06M 13/313* | (2006.01) |
| *D06M 13/364* | (2006.01) |
| *D06M 101/32* | (2006.01) |

(52) U.S. Cl.
CPC ........ *C08K 5/34924* (2013.01); *C08K 5/5373* (2013.01); *C08K 5/5398* (2013.01); *C08L 69/00* (2013.01); *D06M 13/313* (2013.01); *D06M 13/364* (2013.01); *D06M 2101/32* (2013.01); *D06M 2200/30* (2013.01)

(58) Field of Classification Search
USPC .......................................................... 428/480
See application file for complete search history.

(56) References Cited

U.S. PATENT DOCUMENTS

| | | |
|---|---|---|
| 5,420,326 A | 5/1995 | Telschow |
| 2005/0038278 A1 | 2/2005 | Dittrich et al. |

FOREIGN PATENT DOCUMENTS

| | | |
|---|---|---|
| EP | 2284208 | 2/2011 |
| EP | 2557085 | 2/2013 |
| WO | 9104295 | 4/1991 |

OTHER PUBLICATIONS

New Phosphorus-Containing Quinone Derivatives; Patrick Müller et al., Heteroatom Chemistry, vol. 23, No. 4, 2012.
Synthesis and characterization of a DOPO-substitued organophosphorus oligomer and its application in flame retardant epoxy resins; Xin Wang et al., Progress in Organic Coatings 71 (2011) 72-82.
A effective flame retardant for epoxy resins based on poly(DOPO substituted dihydroxyl phenyl pentaerythritol diphosphonate); Xin Wang et al., Materials Chemistry and Physics 2011, 125, 536-541.

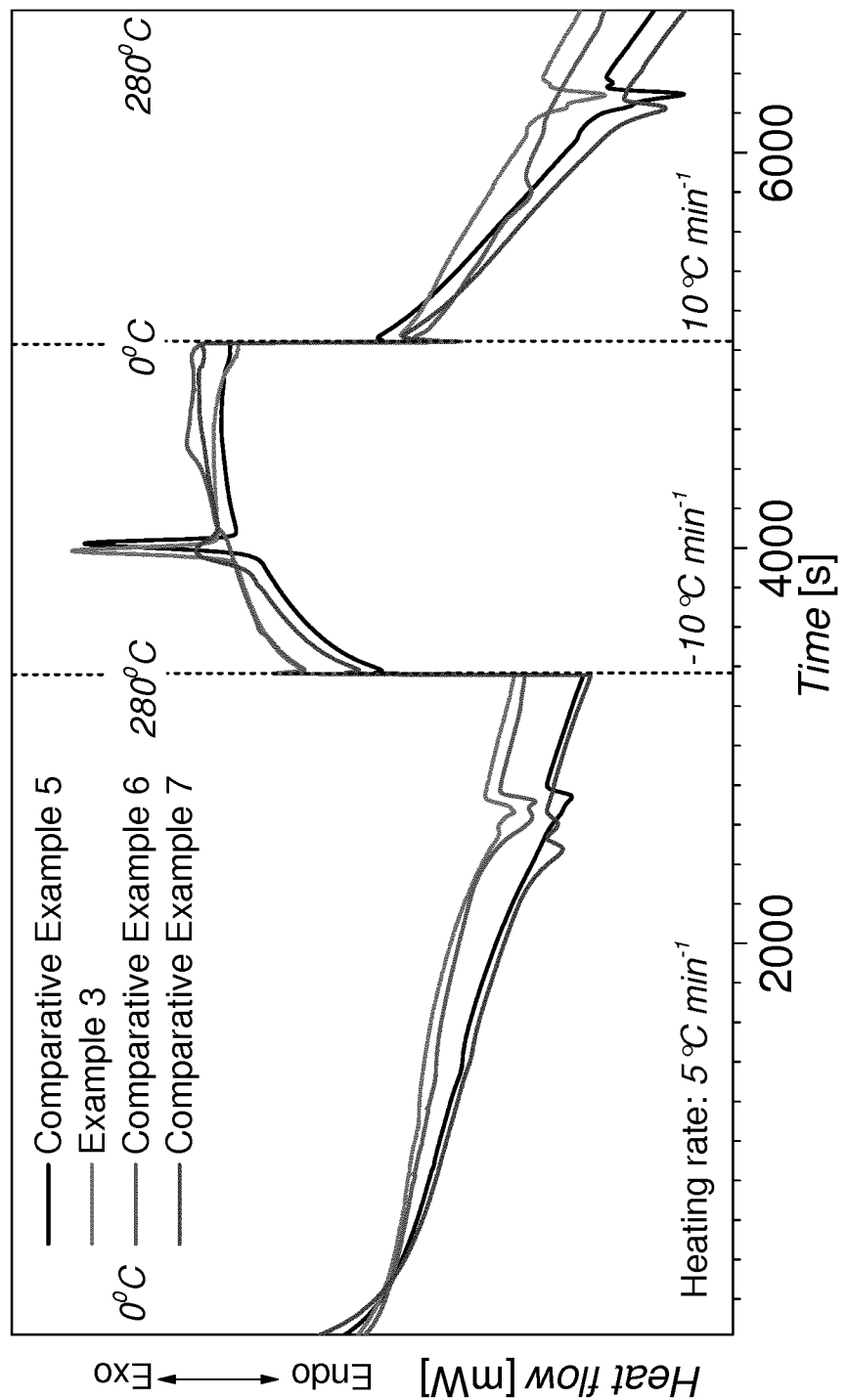

DOPO-BASED HYBRID FLAME RETARDANTS

This application claims priority from PCT application No. PCT/EP2015/055433 filed Mar. 16, 2015 which claims priory from European application No. EP 14160392.8 filed on Mar. 17, 2014, the disclosures of which are incorporated herein by reference.

FIELD OF THE INVENTION

The present invention generally relates to novel flame retardant 9,10-dihydro-9-oxa-10-phosphaphenanthrene compounds.

BACKGROUND OF THE INVENTION

Various phosphorus containing compounds have already been investigated for their suitability as flame retardant additives. In particular, DOPO (9,10-dihydro-9-oxa-phosphaphenanthrene-10-oxide) and derivatives thereof have been explored as flame retardants and are known as predominantly active by a gas-phase flame retardant mechanism.

For example, it is known from EP 1506968 that DOPO-based phosphonates can be synthesized efficiently, whereas U.S. Pat. No. 4,228,064 demonstrates the utility of DOPO-based phosphonates and phosphinates as flame retardant additives for polyphenylene ether formulations. Additionally, EP 2557085 describes the synthesis of DOPO-based phosphonamidates and their application in polyurethane foams.

Furthermore, it is known from DE 10330774 and EP 2284208 that DOPO can be reacted with an unsaturated dicarboxylic acid and subsequently copolymerized with other P-containing derivatives, suitable to build ester bonds, to obtain flame retardant polyesters with varying P-content. These DOPO-based polymers can serve, for example as flame retardant additive for polyethylene terephthalate (PET) in fibre applications or as stand-alone flame retardant polyesters in engineering plastics.

Although the thermal stability of some of the reported DOPO derivatives would enable their melt processing at elevated temperatures as typically used for polyester processing, none of these derivatives were shown to form char upon pyrolysis, a property that would increase their efficacy as flame retardant additives.

Polymers and/or oligomers (no molecular weight is typically reported) containing pentaerythritol diphosphonate, a char former unit, having DOPO as a pendant group, such as reported by Wang X. et all in Materials Chemistry and Physics 2011, 125, 536-541 and the like, are known. However, for all the reported structures the question of having halogenated end-groups is not addressed. This might be an issue, in view of the fact that, for a relatively low molecular weight additive, the significance of the end-groups is increased.

Pentaerythritol phosphate alcohol (PEPA) is known as a flame retardant additive with relatively low thermal stability (decomposition around 200° C.), being active primarily in the condensed-phase, forming up to 40 wt % char upon pyrolysis. Derivatives of PEPA are mostly used as flame retardant additives for polyolefins, such as polypropylene, as described in U.S. Pat. No. 5,420,326.

U.S. Pat. No. 4,801,625 describes PEPA derivatives that in combination with other polymer additives, such as inert gas producing compounds (e.g. melamine) or other phosphorus containing derivatives (e.g. ammonium polyphosphate) render polyolefins flame retardant. WO 91/04295 teaches the use of PEPA derivatives to obtain smoke suppressed unsaturated polyester resin compositions.

SUMMARY OF THE INVENTION

Maybe one of the most important class of synthetic polymers requiring flame resistance are thermoplastic polyesters, with numerous applications as engineering plastics as well as melt-spun fibres. Any flame retardant additive to be added to such polymers should have sufficient thermal stability to withstand the temperatures typically needed for melt processing of the polymer. Accordingly, there is still a need for novel and improved halogen free flame retardants for thermoplastics processed at high temperatures. Such compounds should be efficient in their fire retardant action and should not adversely affect the desired properties of the polymer matrix, such as melt viscosity (processability), mechanical properties or the ability to melt spin fibres.

According to an aspect of the present invention, there is provided a flame retardant compound having the structure of Formula (I):

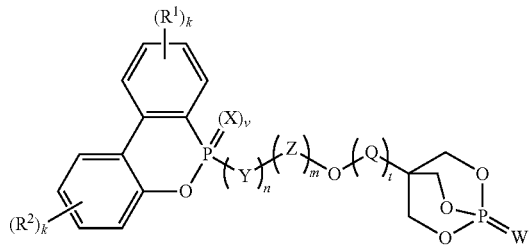

wherein $R^1$ and $R^2$ can independently be hydrogen, $C_1$-$C_6$ alkyl, —$P(O)(OR^3)_2$—$P(O)OR^3R^4$, —$P(O)R^3{}_2$, where $R^3$ and $R^4$ can independently be $C_1$-$C_4$ alkyl, $C_6$-$C_{12}$ aryl, $C_7$-$C_{15}$ aralkyl, $C_7$-$C_{15}$ alkaryl; or $R^1$ and $R^2$ taken together can form an unsaturated cyclic ring, which may be substituted by an alkyl group; each k can independently be an integer from 1 to 2; each X can independently be oxygen (O) or sulphur (S); v can be 0 or 1; each Y can independently be $C_1$-$C_4$ alkylene, $C_6$ arylene, $C_7$-$C_{15}$ aralkylene, $C_7$-$C_{15}$ alkarylene, oxygen (O), nitrogen (NR) wherein R is H or $C_1$-$C_4$ alkyl; n can be 0, 1, or 2 with the proviso that when Y is oxygen (O) or nitrogen (NR) n is 1; each Z can independently be $C_1$-$C_4$ alkylene, $C_6$ arylene, $C_7$-$C_{15}$ aralkylene or $C_7$-$C_{15}$ alkarylene; m can independently be 0, 1, or 2; with the proviso that when Y is oxygen (O) or nitrogen (N), m cannot be 0; each Q can independently be $C_1$-$C_4$ alkylene; t is an integer from 1 to 2; W can be oxygen (O) or sulphur (S).

Advantageous embodiments of the invention are defined in the dependent claims and/or are described herein below.

It was surprisingly found that the above defined compounds, which are based on a combination of DOPO- and PEPA-type moieties and thus could be envisioned as "hybrid flame retardants", exhibit a combination of several characteristics that are highly desirable in a flame retardant compound, particularly in a flame retardant additive for thermoplastic polyesters. Such advantageous properties comprise, but are not limited to, a high thermal stability (enabling melt blending), a high melting temperature of at least about 150° C. and closely lying below the melt processing temperature of most polyesters, thus allowing for a more even dispersion of the additive in the polymer matrix. Preferably the thermal stability of the compounds is from around 270° C. to around 335° C., more preferably from around 280° C. to around 330° C., most preferably from around 290° C. to around 325° C., and the melting temperature is preferably from around 150° C. to around 260° C., more preferably, from around 160° C. to around 240° C., most preferably from around 170° C. to around 230° C. When exposed to a flame or fire the compounds of the present invention exhibit a hybrid flame retardant activity in the gas-phase and in condensed-phase simultaneously. In other words, different flame retardant mechanisms are combined in one molecule and thus can be included in a polymer without the need of admixing two different flame retardant compounds.

It is contemplated that the compounds of the present invention may be useful for improving the flame resistance of certain thermoset polymers.

In particular, however, the compounds of the present invention are useful for making thermoplastic polyester materials with good flame resistance in spite of relatively low additive loading.

Therefore, according to another aspect of the invention there is provided a polymeric material with improved flame resistance, henceforth also called "flame resistant polymeric material", that comprises at least one thermoplastic polymer resin and at least one flame retardant compound having the structure of Formula (I) as defined above, and optionally comprising any conventional additives.

In some embodiments, the thermoplastic polymer resin may be a polyolefin, a polycarbonate or an epoxy resin. According to another embodiment, the thermoplastic polymer resin is a polyester resin.

According to one embodiment, the flame resistant polymeric material may additionally include a nitrogen based flame retardant agent, as a second flame retardant component.

According to one embodiment, the polymeric material is in a form suitable for engineering plastics applications. According to another embodiment, the polymeric material is in fibre form, particularly for textile applications.

In the following, the term "radical" is sometimes used interchangeably with "group" or "moiety" or "substituent", e.g. "alkyl radical" is equivalent to "alkyl group, as customary in organic chemistry.

Unless otherwise indicated, the term "alkyl" as used herein includes saturated monovalent hydrocarbon radicals with straight or branched moieties such as, but not limited to: methyl, ethyl, propyl, isopropyl, butyl or isobutyl.

Unless otherwise indicated, the term "alkylene" as used herein includes saturated divalent hydrocarbon radicals with straight or branched moieties such as, but not limited to: methylene, ethylene, propylene, isopropylene, butylene or isobutylene.

Unless otherwise indicated, the term "aryl" as used herein includes an aromatic radical derived from an aromatic hydrocarbon by removal of one hydrogen, such as, but not limited to, phenyl or naphthyl.

Unless otherwise indicated, the term "arylene" as used herein includes an aromatic bivalent radical derived from an aromatic hydrocarbon by removal of two hydrogens, such as, but not limited to phenylene.

Unless otherwise indicated, the term "aralkyl" as used herein signifies an "aryl-alkyl-" group, such as, but not limited to: benzyl ($C_6H_5$—$CH_2$—) or methylbenzyl ($CH_3$—$C_6H_4$—$CH_2$—).

Unless otherwise indicated, the term "alkaryl" as used herein signifies an "alkyl-aryl-" group, such as, but not limited to: methylphenyl ($CH_3$—$C_6H_4$—), dimethylphenyl (($CH_3$)$_2$—$C_6H_3$—) or isopropylphenyl (($CH_3$)$_2$C—$C_6H_4$—).

Unless otherwise indicated, the term "thermal stability" as used herein in relation to a compound is characterized by indicating a "decomposition temperature", which shall be understood as a threshold temperature at which substantial (5% weight loss under inert atmosphere) thermal decomposition of the compound sets in.

In one embodiment of the flame retardant compound, both n and m are 0, X is independently oxygen (O) or sulphur (S), Q is methylene (—$CH_2$—), t is 1, W is oxygen (O). In another embodiment, both $R_1$ and $R_2$ are independently hydrogen or a $C_1$-$C_6$ alkyl. In another embodiment, Y is methylene (—$CH_2$—), n is 1, m is 0, X is oxygen (O), Q is methylene (—$CH_2$—), t is 1, W is oxygen (O). In yet another embodiment, X independently oxygen (O) or sulphur (S), Y is oxygen (—O—), or nitrogen (—NH—), n is 1, Z is methylene (—$CH_2$—), m is 2, Q is methylene (—$CH_2$—), t is 1, W is oxygen (O).

Specific examples of compounds of Formula (I) that may be used in this invention are:

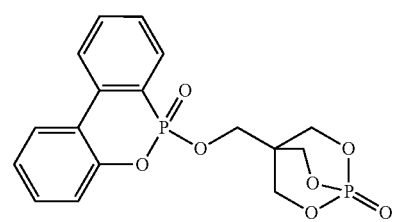

DOPO-PEPA

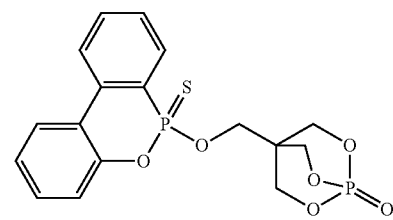

DOPS-PEPA

According to another aspect, a process of making the hybrid flame retardant compounds of Formula (I) comprises reacting a compound of Formula (A):

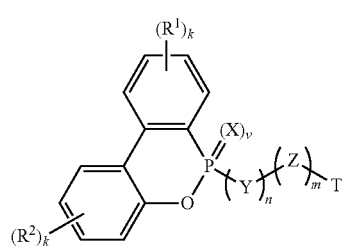

(A)

wherein $R^1$, $R^2$, m, X, v, Y, n and Z are defined above, T can be hydrogen or a halogen selected from Cl, Br or I, with the proviso that when T is hydrogen both n and m are 0, with a compound of Formula (B):

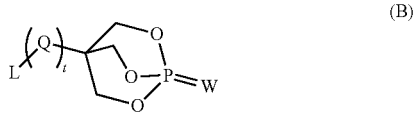
(B)

wherein Q, t, W are defined above and L is a hydroxyl (—OH), in the presence of a base.

The base that may be used is any suitable base, capable of scavenging hydrogen halides in a nucleophilic substitution reaction, such as a tertiary amine. Generally suitable bases include, but are not limited to, triethylamine or N-methylimidazole.

Any suitable amount of base may be used including, from about 1 to about 10 equivalents, or about 1 to about 5 equivalents, based on the amount of compound of Formula A.

The process may optionally be carried out in a solvent. Solvents that may be used include, but are not limited to, chloroform, dichloromethane, tetrahydrofuran, acetonitrile, toluene or mixtures thereof.

The process may be conducted at temperature ranging from about −5° C. to about 110° C.

Another process that may be used to produce a hybrid flame retardant compound of Formula (I) comprises reacting a compound of Formula (A), where $R^1$, $R^2$, m, X, v, Y, n, and Z are defined above, T is hydroxyl (OH) and m cannot be 0, with a compound of Formula B where Q, t, W are defined above and L is a halogen selected from Cl, Br or I, in the presence of a base.

One base that may be used is an alkali metal base, such as alkyl metal alkoxides, alkali metal amides and alkali metal alkyl amides. Examples of bases that may be used include, but are not limited to, sodium methoxide, potassium methoxide, sodium ethoxide, potassium ethoxide, sodium t-butoxide, potassium t-butoxide, lithium diisopropyl amide and mixture thereof.

The process may optionally be carried out in a solvent. Solvents that may be used include, but are not limited to, tetrahydrofuran, acetonitrile, toluene, xylene; N, N-dimethylformamide, N, N-dimethylacetamide, dimethyl sulfoxide or mixtures thereof.

The process may be conducted at temperature ranging from about −5° C. to about 75° C.

It is preferred that the purity of the compounds of Formula (I), when combined with polyesters, should be greater than 95%, more preferably 98% or most preferably 99%.

In the present invention, "thermoplastic polyester resin" is defined as a polyester based on at least an aliphatic or aromatic dihydroxy compound and at least an aromatic dicarboxylic acid. The thermoplastic polyester used in various embodiments is not limited and can vary. Particularly preferred polyesters are polybutylene terephthalate (typically abbreviated as PBT), polyethylene terephthalate (typically abbreviated as PET) and polyethylene naphthalate (typically abbreviated as PEN) or any combination of these. The term "thermoplastic polyester" includes also thermoplastic copolyester elastomers such as, but not limited to copolyether ester (typically abbreviated as COPES, or TPE-E). Other polyesters not specifically described are also encompassed by these embodiments and can be combined with the hybrid flame retardant systems described above to create flame retardant polyesters of the invention. Products of this type are, for example, ULTRADUR® (BASF, PBT) and ARNITEL® (DSM, TPE-E)

The total content of the hybrid flame retardant component according to the present invention can vary among the embodiments of the flame resistant polymeric material, henceforth also abbreviated as "composition", and may be modified based on the desired properties of the flame resistant polymeric material.

For example, in some embodiments, particularly in the case of polymeric materials in the form of granules or in moulded form, the total content of the flame retardant component is preferably lower than 30% by weight of the total weight of the composition, more preferably lower than 25% by weight of the total weight of the composition, and most preferably lower than 20% by weight on the total weight of the composition so that mechanical and electrical properties are satisfactory with respect to most of the desired applications. However, in order to achieve satisfactory flame retardant properties, the total content of the flame retardant component is preferably not lower than 14% by weight of the total weight of the composition.

In other embodiments, particularly in the case of polymeric materials in the form of fibres, the total content of the flame retardant component is preferably lower than 15% by weight on the total weight of the composition, more preferably lower than 10% by weight on the total weight of the composition, even more preferably lower than 7% by weight on the total weight of the composition. However, in order to achieve satisfactory flame retardant properties, the total content of the flame retardant component is preferably higher the 5% by weight on the total weight of the composition.

It will be understood that the flame resistant polymeric material may include additional additives to provide for example colour, or to improve one or more properties exhibited by the flame retardant polyester. Examples of such additional additives include, but are not limited to the following examples: fire resistant additives, processing aids, heat and process stabilizers, UV stabilizers, anti-dripping agents such as, but not limited to: PTFE (polytetrafluoroethylene), pigments, dispersing agents, nucleating agents and other additives typically used with polyesters or polyester fibres. Such additives are often contained in commercially available polymer resins.

In one embodiment, the flame resistant polymeric material further includes a nitrogen based flame retardant agent as a second flame retardant component. Such nitrogen based flame retardant agents are generally known and may include, but are not limited to, symmetric triazine derivatives, complexes and condensation products with high nitrogen content. Particularly suitable nitrogen based flame retardant agents are those with an appropriate thermal stability, which allows their melt processing at temperatures exceeding 200° C. Furthermore, the nitrogen based flame retardant agents must be compatible with the polyester resin and with the other additive components applied in this invention. Additionally, they should not migrate to the surface when incorporated in the polyester resin, they should be available in fine particle size distribution suitable for melt processing and they should not cause discoloration or odor when incorporated in the polyester resin.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein:

FIG. 1 shows DSC curves of the Arnitel® products and Arnitel® 622+Example 1 (14 wt %).

DETAILED DESCRIPTION OF THE INVENTION

Examples

The following examples illustrate the present invention. It is to be understood, however, that the invention as described herein and as recited in the claims is not intended to be limited by the details of the following Examples.

Example 1

Synthesis of DOPO-PEPA

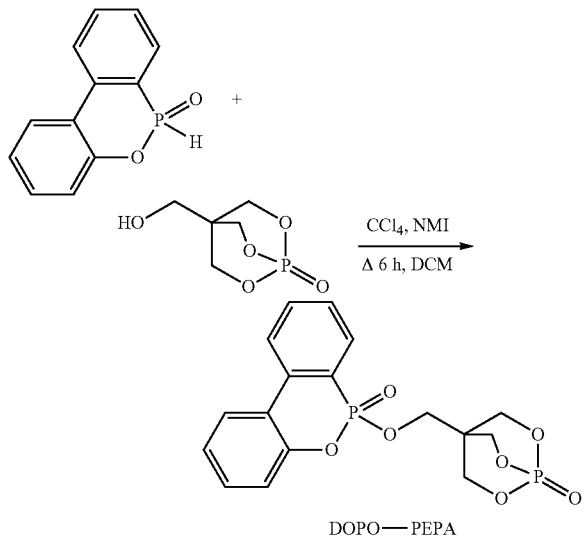

DOPO—PEPA

In this example 500 g 9,10-dihydro-9-oxa-phosphaphenanthrene-10-oxide (DOPO) and 458 g pentaerythritol phosphate alcohol (PEPA) was placed in 1.5 L dichloromethane (DCM). 221 mL N-methyl imidazole (NMI) was added to the stirring suspension followed by 248 mL carbon tetrachloride ($CCl_4$) added drop-wise, over a period of 1 h. During the addition of $CCl_4$, the temperature was kept between 15°–20° C. Subsequently, the reaction mixture was refluxed for 6 h. After cooling down, the dichloromethane was distilled under vacuum and the product was precipitated out with water (2 L). After stirring for 3 hours the product was filtered as a white powder and dried at 60° C. under vacuum to a constant weight, yielding 744 g (82%) DOPO-PEPA.

Melting point: m.p.=222° C. (based on DSC, heating rate=5° C. $min^{-1}$)

Thermal stability: $T_{5\%}$=338° C.; $T_{63\%}$=700° C.

Phosphorus content: 15.71 wt %

$^1$H-NMR, δ (ppm): 3.98-4.09 (m, 2H); 4.48 (d, =6.5 Hz,); 7.34-7.40 (m, 2H), 7.51 (t, 7.7 Hz, 1H); 7.65 (dt, J=3.8 Hz, J=7.4 Hz, 1H); 7.85-7.95 (m, 2H); 8.20-8.27 (m, 2H)

$^{13}$C-NMR, δ (ppm): 37.48, 61.87, 75.02, 119.95, 120.65, 121.92, 124.86, 125.39, 126.03, 128.91, 130.03, 131.06, 134.41, 136.35, 148.87.

$^{31}$P-NMR, δ (ppm): −7.18; 10.96.

Example 2

Synthesis of DOPS-PEPA

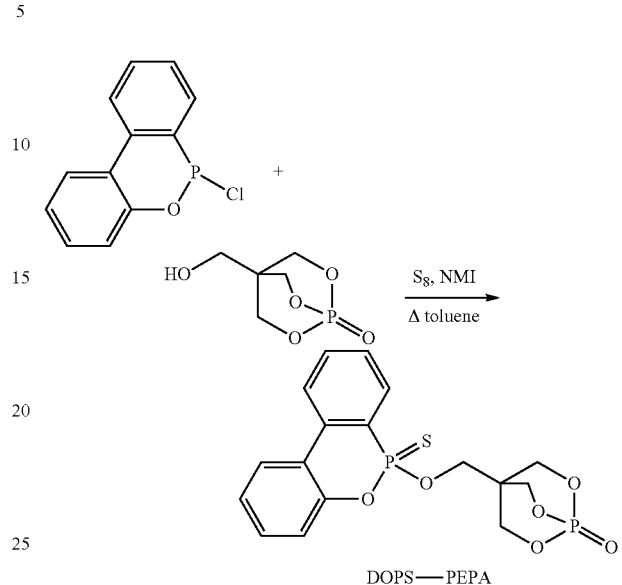

DOPS—PEPA

In this example, the suspension of 10 g 6-chloro-6H-dibenzo[c,e][1,2]oxaphosphinine (DOP-Cl) and 1.6 g $S_8$ in 100 mL toluene was heated to reflux for 5 h. After cooling it to room temperature, 3.7 mL N-methyl imidazole (NMI) was added followed by 8.4 g pentaerythritol phosphate alcohol (PEPA). The temperature was kept between 15°-20° C. during the addition. Subsequently, the reaction mixture was refluxed for 3 h. After cooling it to room temperature, the precipitated product was filtered, washed with water (2×300 mL) and alcohol (2×300 mL). The obtained white powder was dried at 60° C. under vacuum to a constant weight, yielding 12.3 g (70%) DOPS-PEPA.

Melting point: m.p.=200° C. (based on DSC, heating rate=5° C. $min^{-1}$)

Thermal stability: $T_{5\%}$=296° C.; $T_{64\%}$=700° C.

Phosphorus content: 15.10 wt %

$^1$H-NMR, δ (ppm): 3.99-4.09 (m, 2H); 4.33-4.42 (m,); 7.36-7.41 (m, 2H), 7.52 (t, =8.0 Hz, 1H); 7.63-7.67 (m, 1H); 7.85 (t, =8.0 Hz, 1H); 7.95-8.02 (m, 1H), 8.18-8.22 (m, 2H)

$^{13}$C-NMR, δ (ppm): 37.28, 61.83, 74.94, 119.96, 122.24, 124.73, 125.10, 125.58, 126.03, 128.93, 130.81, 131.02, 134.13, 134.35, 148.77.

$^{31}$P-NMR, δ (ppm): −7.27; 77.03.

Examples 3 and 4

Flame Retardant TPE-E (Arnitel 622®)

Melt Processing:

Various Arnitel® compositions were prepared on a co-rotating twin screw extruder (Haake Polylab OS, model PTW 24/40, Germany) with a screw diameter of 24 mm and a L/D ratio of 40. Dosing of the materials was performed using a gravimetric feeding system (Three Tec, Switzerland). All compositions were processed at identical screw rotational speed. The measured temperature of the melt was 230° C. for all the formulations. The composite melt was passed through a nozzle, cooled to room temperature in a water bath and cut into granules. The granules were dried at 100° C. for 12 hours in a vacuum oven. The analysed granules were conditioned at 50% relative humidity for 72 hours.

The resulting compounds were as follows:

Example 3: Arnitel CM622® with 18 wt % DOPO-PEPA (Example 1) (2.8 wt % P-content), m.p.=224° C.

Example 4: Arnitel CM622® with 14 wt % DOPO-PEPA (Example 1) (2.2 wt % P-content), m.p.=224° C. and 4 wt % Melapur MC 50 (melamine cyanurate)

Comparative Example 5: Arnitel CM622® containing no flame retardant additive (0 wt % P-content), m.p.=218° C.

Comparative Example 6: Arnitel LX07000® containing a halogenated flame retardant additive (0 wt % P-content), m.p.=226° C.

Comparative Example 7: Arnitel CM600® containing a nitrogen based flame retardant additive (0 wt % P-content), m.p.=216° C.

ASTM D3801 UL94—Vertical Burning Test

The dried granules were compression moulded into 1 mm thick plates and cut to the dimensions (125±5 mm long by 13.0±0.5 mm wide) required by the ASTM D3801 UL94—Vertical Burning Test (V-0, V-1, or V-2).

TABLE 1

UL94 Vertical burning tests

| Compositions | Rating |
| --- | --- |
| Comparative Example 5 | No rating |
| Comparative Example 6 | V2 |
| Comparative Example 7 | V2 |
| Example 3 | V0 |
| Example 4 | V0 |

Differential Scanning Calorimetry (DSC)

Differential scanning calorimetry measurements were carried out to evaluate the Arnitel® formulations (FIG. 1). The first heating cycle (using a heating rate of 5° C. min$^{-1}$) was used to assess the melting point of the compounds as reported above. After cooling down with a cooling rate of 10° C. min$^{-1}$ the formulations were heated again at a heating rate of 10° C. min$^{-1}$. In the second heating cycle, only the composition of Example 3 revealed identical melting point with the pristine TPE (Comparative Example 5). The decrease of the melting temperature of a thermoplastic composition in the second heating cycle strongly suggests a deterioration of the molecular weight of the thermoplastic segment and therefore a drop in its desired mechanical and physical properties. These measurements indicate the good compatibility and no adverse effect of the additive of Example 1 on the polymer matrix. Resistance to elevated temperatures of the Arnitel® compositions is important in view of their major application in the automotive industry for under the hood applications and from recyclability point of view.

Example 8

Flame Retardant PET Fibres

Ready-to-spin PET granules, with a viscosity of 1.40 g cm$^{-3}$ were premixed with 5 wt % of the hybrid flame retardant from Example 1 and introduced in a spinneret, through a hopper, comprising a single screw extruder with a diameter of 13 mm and a length-to-diameter (L/D) ratio of 25. A monofilament spinneret was used with a diameter of 0.5 mm and a length-to-diameter (L/D) ratio of 4. The PET compositions were spun having a melt temperature of 270° C. and at a winding speed of 1650 m min$^{-1}$. The monofilament PET compositions obtained with a draw ration of 5.5, were having a diameter of ø=59 µm and fibre linear densities of 36 dtex. The obtained flame retardant PET fibre (Example 8) has a corresponding P-content of 0.8 wt %, whereas Comparative Example 9 was prepared as a control example without added flame retardant.

The physical properties of the fibres are listed in Table 2. Comparative Example 9 is the control sample.

TABLE 2

Physical properties of flame retardant PET fibre Example 8 and Comparative Example 9

| PET Fibre | Tenacity (cN/tex) | Elongation (%) | P-content (wt %) | UL94 Rating |
| --- | --- | --- | --- | --- |
| Example 8 | 44.67 (±1.59) | 18.34 (±3.55) | 0.8 | V0 |
| Comparative Example 9 | 46.19 (±1.13) | 18.63 (±2.55) | 0 | V2 |

For the evaluation of the fire resistance, the PET fibres were knitted into a fabric with a density of 0.13±0.03 g cm$^{-2}$. Five samples, with a length of 10 cm, were cut out from each Example, having an average weight of 1±0.02 g. The 100±5 mm long tightly rolled samples were subjected to vertical burning tests following the testing procedure and materials classifications as described in ASTM D3801 UL94—Vertical Burning Test (V-0, V-1, or V-2) and the results are listed in Table 2.

Example 10

Flame Retardant PBT (ULTRADUR®)

Various Ultradur® compositions were prepared on a co-rotating twin screw extruder (Haake Polylab OS, model PTW 24/40, Germany) with a screw diameter of 24 mm and a L/D ratio of 40. Dosing of the materials was performed using a gravimetric feeding system (Three Tec, Switzerland). All the compositions were processed at identical screw rotational speed. The composite melt was passed through a nozzle, cooled to room temperature in a water bath and cut into granules. The granules were dried at 80° C. for 12 hours in a vacuum oven. The analysed granules were conditioned at 50% relative humidity for 72 hours.

The resulting compounds were as follows:

Example 10: Ultradur® with 20 wt % DOPO-PEPA (Example 1) (3.2 wt % P-content) and 4.5 wt % Melapur MC 50 (melamine cyanurate)

Comparative Example 11: Ultradur® containing no flame retardant additive (0 wt % P-content)

ASTM D3801 UL94—Vertical Burning Test

The dried granules were compression moulded into 1 mm thick plates and cut to the dimensions (125±5 mm long by 13.0±0.5 mm wide) required by the ASTM D3801 UL94—Vertical Burning Test (V-0, V-1, or V-2).

TABLE 1

UL94 Vertical burning tests

| Compositions | Rating |
| --- | --- |
| Comparative Example 11 | No rating |
| Example 10 | V0 |

The invention claimed is:

1. A flame retardant compound having the structure of Formula I:

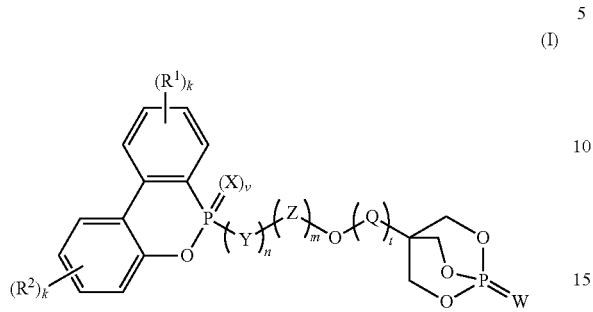

(I)

wherein:
R¹ and R² are independently hydrogen, $C_1$-$C_6$ alkyl, —P(O)(OR³)$_2$, —P(O)OR³R⁴, or —P(O)R³$_2$, wherein R³ and R⁴ are independently $C_1$-$C_4$ alkyl, $C_6$-$C_{12}$ aryl, $C_7$-$C_{15}$ aralkyl or $C_7$-$C_{15}$ alkaryl; or R¹ and R² taken together form an unsaturated cyclic ring, which is optionally substituted by an alkyl group;
each k is independently an integer from 1 to 2;
each X is independently oxygen (O) or sulphur (S);
v is 0 or 1;
each Y is independently $C_1$-$C_4$ alkylene, $C_6$ arylene, $C_7$-$C_{15}$ aralkylene, $C_7$-$C_{15}$ alkarylene, oxygen (O), nitrogen (NR), wherein R is H or $C_1$-$C_4$ alkyl;
n is 0, 1 or 2 with the proviso that n is 1 when Y is oxygen (O) or nitrogen (NR);
each Z is independently $C_1$-$C_4$ alkylene, $C_6$ arylene, $C_7$-$C_{15}$ aralkylene or $C_7$-$C_{15}$ alkarylene;
m is independently 0, 1 or 2; with the proviso that when Y is oxygen (O) or nitrogen (N), m cannot be 0;
each Q is independently $C_1$-$C_4$ alkylene;
t is an integer from 1 to 2;
W is oxygen (O) or sulphur (S).

2. A flame retardant compound according to claim 1, selected from the group consisting of:
DOPO-PEPA, and
DOPS-PEPA.

3. A polymeric material with improved flame resistance, comprising at least one thermoplastic polymer resin, at least one flame retardant compound according to claim 1, and optionally any conventional additives.

4. The polymeric material according to claim 3, wherein the thermoplastic polymer resin is a thermoplastic polyester resin.

5. The polymeric material according to claim 3, further comprising a nitrogen based flame retardant agent, as a second flame retardant component.

6. The polymeric material according to claim 3, in the form of granules or in moulded form.

7. The polymeric material according to claim 6, wherein the total content of the flame retardant component (I) is 14% to 30% by weight of the total weight of the composition.

8. The polymeric material according to claim 3, in the form of fibres.

9. The polymeric material according to claim 8, wherein the wherein the total content of the flame retardant component (I) is 5% to 20% by weight of the total weight of the composition.

10. The polymeric material according to claim 3, wherein the flame retardant compound is deposited as a surface layer.

11. A method of making a flame retardant compound according to claim 1, the method comprising reacting compound of Formula (A):

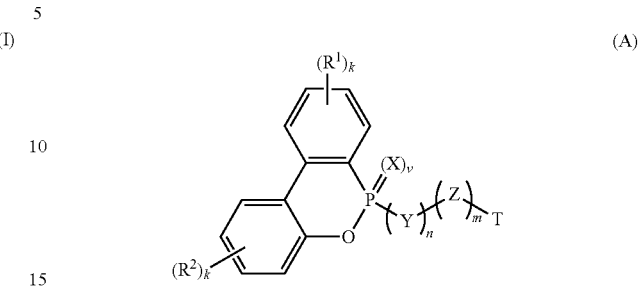

(A)

with a compound of Formula (B):

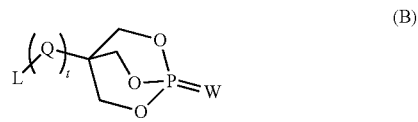

(B)

in the presence of a base, wherein:
a) R¹, R², m, X, v, Y, n and Z are defined above, T can be hydrogen or a halogen selected from Cl, Br or I, with the proviso that when T is hydrogen both n and m are 0, and wherein Q, t, W are defined above and L is a hydroxyl (—OH); or:
b) R¹, R², m, X, v, Y, n and Z are defined above, T is hydroxyl (OH) and m is different than 0, and wherein Q, t, W are defined above and L is a halogen selected from Cl, Br or I.

12. A polymeric material with improved flame resistance, comprising at least one thermoplastic polymer resin, at least one flame retardant compound according to claim 2, and optionally any conventional additives.

13. The polymeric material according to claim 12, wherein the thermoplastic polymer resin is a thermoplastic polyester resin.

14. The polymeric material according to claim 12, further comprising a nitrogen based flame retardant agent, as a second flame retardant component.

15. The polymeric material according to claim 13, further comprising a nitrogen based flame retardant agent, as a second flame retardant component.

16. The polymeric material according to claim 4, further comprising a nitrogen based flame retardant agent, as a second flame retardant component.

17. The polymeric material according to claim 4, in the form of granules or in moulded form.

18. The polymeric material according to claim 17, wherein the total content of the flame retardant component (I) is 14% to 30% by weight of the total weight of the composition.

19. The polymeric material according to claim 5, in the form of granules or in moulded form.

20. The polymeric material according to claim 19, wherein the total content of the flame retardant component (I) is 14% to 30% by weight of the total weight of the composition.

* * * * *

UNITED STATES PATENT AND TRADEMARK OFFICE
CERTIFICATE OF CORRECTION

PATENT NO. : 10,072,212 B2
APPLICATION NO. : 15/126433
DATED : September 11, 2018
INVENTOR(S) : Timea Stelzig et al.

Page 1 of 1

It is certified that error appears in the above-identified patent and that said Letters Patent is hereby corrected as shown below:

In the Specification

Column 7, Line 64, delete "13C-NMR" and insert --$^{13}$C-NMR--.

In the Claims

Column 11, Claim 9, Line 1, delete "wherein", second occurrence.

Signed and Sealed this
Twentieth Day of November, 2018

Andrei Iancu
*Director of the United States Patent and Trademark Office*